United States Patent
Egermann et al.

(10) Patent No.: US 7,464,582 B2
(45) Date of Patent: Dec. 16, 2008

(54) METHOD FOR DETERMINING THE INLET CAPILLARY PRESSURE OF A POROUS MEDIUM

(75) Inventors: Patrick Egermann, Rueil Malmaison (FR); Jean-Marc Lombard, Rueil Malmaison (FR); Pierre Bretonnier, Houilles (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 137 days.

(21) Appl. No.: 11/514,228

(22) Filed: Sep. 1, 2006

(65) Prior Publication Data
US 2007/0062258 A1    Mar. 22, 2007

(30) Foreign Application Priority Data
Sep. 5, 2005    (FR)    ................... 05 09041

(51) Int. Cl.
*G01N 15/08*    (2006.01)
(52) U.S. Cl. .......................................... 73/38
(58) Field of Classification Search .............. 73/38
See application file for complete search history.

(56) References Cited

U.S. PATENT DOCUMENTS

| 4,893,504 A | 1/1990 | O'Meara, Jr. et al. |
| 5,245,859 A | 9/1993 | Smith et al. |
| 5,311,766 A | 5/1994 | Persoff et al. |
| 6,021,662 A | 2/2000 | Moulu et al. |

OTHER PUBLICATIONS

Hildenbrand A. et al.; "Gas Breakthrough Experiments on Fine-grained Sedimentary Rocks", Geofluids, vol. 2, Aug. 30, 2001, pp. 3-23.

*Primary Examiner*—Daniel S Larkin
(74) *Attorney, Agent, or Firm*—Antonelli, Terry, Stout & Kraus, LLP.

(57) ABSTRACT

To perform at least an evaluation of the inlet capillary pressure value of a porous medium. From a displacement experiment on a sample of the medium, a curve of the volume of saturating fluid expelled from the sample as a function of time is drawn. The differential pressure between the inlet face and at least one point located at a distance Li from the inlet face that is greater than the distance between the inlet face and the interface between the two fluids within the sample is then continuously measured as a function of time. At least one motive pressure gradient of the first fluid is thereafter calculated by means of distance Li and of the curve. Finally, at least one value of the inlet capillary pressure is determined by calculating the difference between the differential pressure and the value of the motive pressure gradient of the expelled fluid. The method can be applied notably to production of oil reservoirs for example.

13 Claims, 3 Drawing Sheets

METHOD FOR DETERMINING THE INLET CAPILLARY PRESSURE OF A POROUS MEDIUM

FIELD OF THE INVENTION

The present invention relates to a method allowing one to determine at least one value for the inlet capillary pressure of a porous medium.

The method can notably be applied under operating conditions representative of geologic formations, as regards the nature of the fluids as well as the thermodynamic pressure and temperature conditions.

The potential applications of this method relate in particular to the characterization of low-permeability porous media, such as the cap rocks of an underground reservoir, within the scope of the evaluation of geologic formations as storage sites for fluids, such as hydrocarbons, $CO_2$ or other fluids.

BACKGROUND OF THE INVENTION

The following documents, mentioned in the course of the description hereafter, illustrate the state of the art:

Chiquet O., Broseta D. and Thibeau S., «*Capillary alteration of shaly caprocks by carbon dioxide*», SPE 94183, 14$^{th}$ Europec Conference, Madrid, Spain, 13-16 Jun. 2005;

Hildenbrand, A., Schlömer S., and Krooss B., «*Gas breakthrough experiments on fine-grained sedimentary rocks*», Geofluids Vol. 2, 3-23, 2002;

Monicard R., «*Caractéristiques des roches réservoir—Analyse des carottes*», Paris, France, Éditions Technip, 1981; and Zweigel P. et al., «*Towards a methodology for top seal efficacy assessment for underground CO2 storage*», 7$^{th}$ International Conference on Greenhouse Gas Control Technologies, Vancouver, 5-9 Sep. 2004.

A geologic formation capable of keeping fluids (hydrocarbons for oil reservoirs, $CO_2$ or other gases for storage sites, . . . ) consists of a reservoir rock allowing one to collect fluids coming from a source (mother rock or injection) and of an impervious cap rock located above (at the top) of the reservoir and allowing one to prevent migration of the fluids from the reservoir to the surface. This geologic formation is then referred to as geologic trap.

The capacity of a geologic formation to store fluids, such as hydrocarbons or $CO_2$ for example mainly depends on the morphology of the geologic trap and on the petrophysical properties of the rocks that make up the cap layer.

In general terms, the morphology of a geologic trap is evaluated by means of a geologic characterization based on geophysical data (seismic data for example), and also on data from the wells drilled in the zone (logs, cores and drill cuttings analysis, . . . ). If the geologic formation selected is not located in too hilly a zone, this type of study generally allows one to precisely determine the shape and the extent of the geologic trap.

Petrophysical characterization of the cap rocks requires specific laboratory experiments that can be very long considering the low permeability of such media (typically below 10$^{-6}$ mD). The permeability of a porous medium corresponds to its capacity to allow a fluid (liquid or gas) to flow under the effect of a pressure gradient. Among all the petrophysical properties, it is by far the inlet capillary pressure that plays the most important part in the capacity of cap rocks to maintain the fluids in the reservoir since it controls the allowable maximum storage overpressure at the top of the reservoir. In the literature, the inlet capillary pressure is also referred to as threshold capillary pressure or breakthrough pressure.

What is referred to as inlet capillary pressure is the minimum pressure difference to be imposed between a non-wetting phase and a wetting phase for the non-wetting phase to be able to start saturating the porous medium considered. The inlet capillary pressure is denoted by $P_c^E$.

The significance of the value of the inlet capillary pressure is illustrated on the reservoir scale within the scope of $CO_2$ storage: we consider the case of an aquifer wherein $CO_2$ is injected so as to reduce the emissions discharged to the atmosphere. During storage, the injected $CO_2$ whose density is under usual thermodynamic conditions lower than that of the water in place progressively forms a pocket located in the upper part of the reservoir. At the lower boundary of the pocket (water/$CO_2$ interface), the pressures in each one of the water and $CO_2$ phases are equal since the capillary pressure curve of the reservoir rocks does not generally exhibit a high inlet capillary pressure because these rocks have the property of readily accommodating fluids. Each one of the two phases having a different density, the pressure gradient is also different, which leads to the existence of a pressure difference between the two phases as shown in FIG. 1. This pressure difference is directly related to a height h measured above the water/$CO_2$ interface. FIG. 1 illustrates the pressure difference for two heights $h_1$ and $h_2$ of the water/$CO_2$ interface. The abscissas represent pressures P,$P_{CO2}$ for the $CO_2$ and $P_W$ for the pressure in the water phase. The ordinates represent height h above the interface. In the first case, the interface is at a depth point $C_{f1}$. At depth point $C_x$, height h above the interface is $h_1$. The difference between the pressures is $P_C(h_1)$. In the second case, the interface is at a depth point $C_{f2}$. At depth point $C_x$, height h above the interface is $h_2$. The difference between the pressures is $P_C(h_2)$. Within the scope of a $CO_2$ storage operation, height h above the interface changes from $h_2$ to $h_1$. FIG. 1 thus shows an increase in the pressure difference imposed on the top with time, within the scope of a $CO_2$ storage operation.

In general terms, we write: $P_{CO2}(h) - P_W(h) = (\rho_W - \rho_{CO2}) gh = P_c(h)$ with:

h: the height above the water/$CO_2$ interface $P_{CO2}(h)$: the pressure in the $CO_2$ phase for a height h $P_W(h)$: the pressure in the water phase for a height h $\rho_{CO2}$: density of the $CO_2$ $\rho_W$: density of the water g: gravity $P_c(h)$: the capillary pressure corresponding to a height h.

This pressure difference directly corresponds to the notion of capillary pressure. This capillary pressure $P_c(h)$ furthermore controls the value of the saturation for a given height h. $P_c(h)$ increases as a function of h as shown in FIG. 1: the greater h, the higher the $CO_2$ pressure. The maximum capillary pressure in the reservoir is thus reached at the reservoir top (h=H). This value is denoted by $P_c^T = P_c(H)$. Since capillary continuity is provided at the reservoir/cap rocks interface, the value of the capillary pressure at the top $P_c^T$ is therefore also imposed on the cap rock. Two cases can then arise:

the capillary pressure at the reservoir top is lower than the inlet capillary pressure ($P_c^T < P_c^E$): the $CO_2$ remains confined;

the capillary pressure at the reservoir top is higher than the inlet capillary pressure ($P_c^T > P_c^E$): the $CO_2$ starts circulating in the cap rock and the water saturation in the cap layer will tend towards the value corresponding to $P_c^T$.

In practice, within the scope of fluid injections in an underground reservoir, it is advisable to take a given margin in relation to the value of the capillary pressure at the reservoir top calculated from H because the injection itself can generate dynamic overpressures that can locally lead to capillary pressures at the top that are higher than the calculated capillary pressure at the top ($P_c^T$).

The previous reminder shows how important it is to properly evaluate the value of the inlet capillary pressure of a porous medium, for example within the scope of the storage of fluids, such as hydrocarbons, $CO_2$ or other fluids, in geologic traps.

There are various methods for evaluating the inlet capillary pressure $P_c^E$ of a porous medium for the storage conditions (thermodynamic conditions and nature of the fluids).

There is, for example, a known technique based on the mercury porosimetry method. This method consists in converting a capillary pressure curve obtained by mercury porosimetry for the reservoir conditions by means of the following conversion formula (Monicard, 1981):

$$P_c^E(s) = P_c^E(m) \frac{\sigma_s \cos \theta_s}{\sigma_m \cos \theta_m}$$

with:
$\sigma_m$: mercury/air interfacial tension=480 mN/m
$\theta_m$: mercury/air contact angle=140°
$\sigma_s$: interfacial tension for the fluids considered in the reservoir (typically $CO_2$/brine within the scope of $CO_2$ storage)
$\theta_s$: contact angle for the fluids considered in the reservoir (typically $CO_2$/brine within the scope of $CO_2$ storage)
$P_c^E(s)$: value of the inlet capillary pressure under storage conditions
$P_c^E(m)$: value of the inlet capillary pressure for the mercury porosimetry measurement conditions under ambient conditions.

Although this method allows very fast estimation of a value for the inlet capillary pressure under storage conditions, the representativity thereof can be affected because of the uncertainty as regards the wettability phenomena (contact angle $\theta_{storage}$). Since the value of the contact angle is generally not known, it is selected equal to zero, which corresponds to a perfect wettability of the fluid in place. Recent experimental measurements have shown that this hypothesis could turn out to be erroneous in particular in the case of geologic storage of $CO_2$ (Chiquet et al., 2005). This approach can lead to significant errors in the calculation of the inlet capillary pressure.

There is also another approach, referred to as "conventional" approach, whose principle is based on the very definition of the inlet capillary pressure. This method is for example described by Monicard (1981).

During this approach, the sample to be studied is first saturated and placed in a containment cell, which allows one to work under imposed pressure and temperature conditions. The inlet end piece of the cell is then swept so as to bring the non-wetting fluid, such as $CO_2$ for example, for which the inlet capillary pressure is sought, just in contact with the face of the sample. A device allowing one to measure small liquid productions (either by weighing the liquids produced or by direct measurement from a fine capillary tube) is then set at the level of the outlet end piece.

The experiment then consists in increasing the pressure of the non-wetting fluid at the inlet face in successive increasing stages while monitoring the production level of the fluid saturating the sample at the outlet. The value of the inlet capillary pressure of the rock in relation to the two fluids used then corresponds to the imposed pressure for which production start of the fluid in place has been observed.

Although the principle is simple, implementation of this type of experiment is however delicate within the scope of cap rock evaluation, for the following reasons:

Length: the number of stages before the desired threshold is reached can be large since, in many cases, no realistic approximations are available before the experiment is started. On the other hand, the required waiting time for each pressure plateau is generally rather long to allow effective detection of the production at the outlet; and Accuracy: in the vicinity of the inlet capillary pressure, the non-wetting fluid invasion kinetics is particularly slow because its mobility threshold is then reached, which makes its outlet flow rate extremely low and therefore difficult to detect, all the more so since the rock studied is of low permeability.

The conventional approach thus leads to very long experiment times and rather to an overestimation of the inlet capillary pressure because of a wrong detection of the mobility threshold.

Another technique is the residual capillary pressure approach. This approach was recently proposed (Hildenbrand, 2002) to provide a faster experimental alternative in relation to the conventional approach. The porous medium test cell is prepared in the same way as for the conventional method, but it is placed between two cells C1 and C2 arranged on either side and containing the non-wetting fluid. A valve initially separates cell C1 from the sample which is however in contact with cell C2. A pressure P1 is initially imposed in C1 and a lower pressure P2 is imposed in C2 by seeing to it that the difference between the two pressures is greater than the estimated value of the capillary pressure sought.

The valve is then opened while recording the evolution of P1 and P2. A progressive decrease, then a stabilization is observed for P1 in the course of time, which corresponds to a circulation of the non-wetting fluid towards C2 through the sample. Similarly, pressure P2 increases, then stabilizes. A residual differential pressure is experimentally observed between the two cells, which is interpreted as the inlet capillary pressure of the rock in relation to the fluids studied. Within the scope of this approach, it is also possible to keep P1 constant and to monitor the evolution of P2 only in the course of time.

This approach aroused a real fad as it was published because of the rapidity thereof and of the ease of interpretation. However, recent work has shown that it is risky to directly interpret the differential pressure measured at the end of the experiment directly in terms of inlet capillary pressure (Zweigel et al., 2005). In fact, during the experiment, the upstream part of the sample undergoes an initial drainage stage during circulation of the wetting fluid, then an imbibition stage as the differential pressure progressively decreases. The measured residual pressure therefore corresponds to a pressure at the end of an imbibition stage and not to a pressure at the start of a drainage stage like the inlet capillary pressure. Now, many experimental findings show that these two pressures are generally not equal, the differential pressure at the end of the imbibition stage being systematically lower than the inlet capillary pressure. Although interpretation of the results of this method a priori affords many advantages, it leads, as it is currently considered, to a systematic underestimation of the inlet capillary pressure value.

In relation to the methods currently used and described above, the method according to the invention allows one to obtain a result rapidly, as regards acquisition of the necessary experimental data as well as their interpretation in terms of inlet capillary pressure.

SUMMARY OF THE INVENTION

The invention relates to a method allowing one to perform at least an evaluation of the inlet capillary pressure value of a porous medium, from a displacement experiment wherein a first fluid saturating a sample of said medium is caused to flow by injection of a second fluid at the level of a face of the sample referred to as "inlet" face.

The method comprises the following stages:
applying to the sample a constant pressure allowing said second fluid to flow into said sample,
drawing a curve of the volume of the first fluid expelled from said sample as a function of time;
continuously measuring as a function of time a local differential pressure $DP_t^i$ between said inlet face and at least one point located at a distance $L_i$ from the inlet face, this distance being greater than the distance between said inlet face and an interface between the two fluids within the sample;
calculating at least one differential pressure of the first fluid $DP_w^i$ by means of distance $L_i$ and of said curve
determining at least one inlet capillary pressure value from local differential pressure $DP_t^i$ and the differential pressure value $DP_w^i$ of the first fluid.

The inlet capillary pressure value can be defined as the difference between local differential pressure $DP_t^i$ and the differential pressure value $DP_w^i$ of the first fluid.

According to the method, the differential pressure value $DP_w^i$ of the first fluid can be calculated after a slope change of said curve and by determining this new slope.

According to an embodiment, distance $L_i$ is equal to the length of the sample and only the total differential pressure $DP_t$ between said inlet face and an opposite face of the sample is then measured.

According to another embodiment, distance $L_i$ is smaller than the length of the sample, and the position of the interfaces between the two fluids can be determined by means of local saturation measurements along the sample. Several inlet capillary pressure values can thus be determined and an uncertainty on the value of this inlet capillary pressure can be deduced therefrom.

According to the invention, it may be wise to leave a volume of first fluid upstream from the sample prior to starting injection of the second fluid. Furthermore, the total imposed differential pressure, the temperature of the fluids and the nature of the fluids can allow to restore conditions representative of oil reservoirs or of fluid storage sites.

Within the scope of gas storage for example, and notably within the scope of $CO_2$ storage, the first fluid can be water and the second fluid a gas.

Finally, the method can be applied to a porous medium of reservoir cap type so as to evaluate the storage capacity of a storage reservoir intended for a gaseous fluid, a hydrocarbon or $CO_2$ for example.

BRIEF DESCRIPTION OF THE FIGURES

Other features and advantages of the method according to the invention will be clear from reading the description hereafter of embodiments given by way of non limitative example, with reference to the accompanying figures wherein.

DETAILED DESCRIPTION

Figure 1:
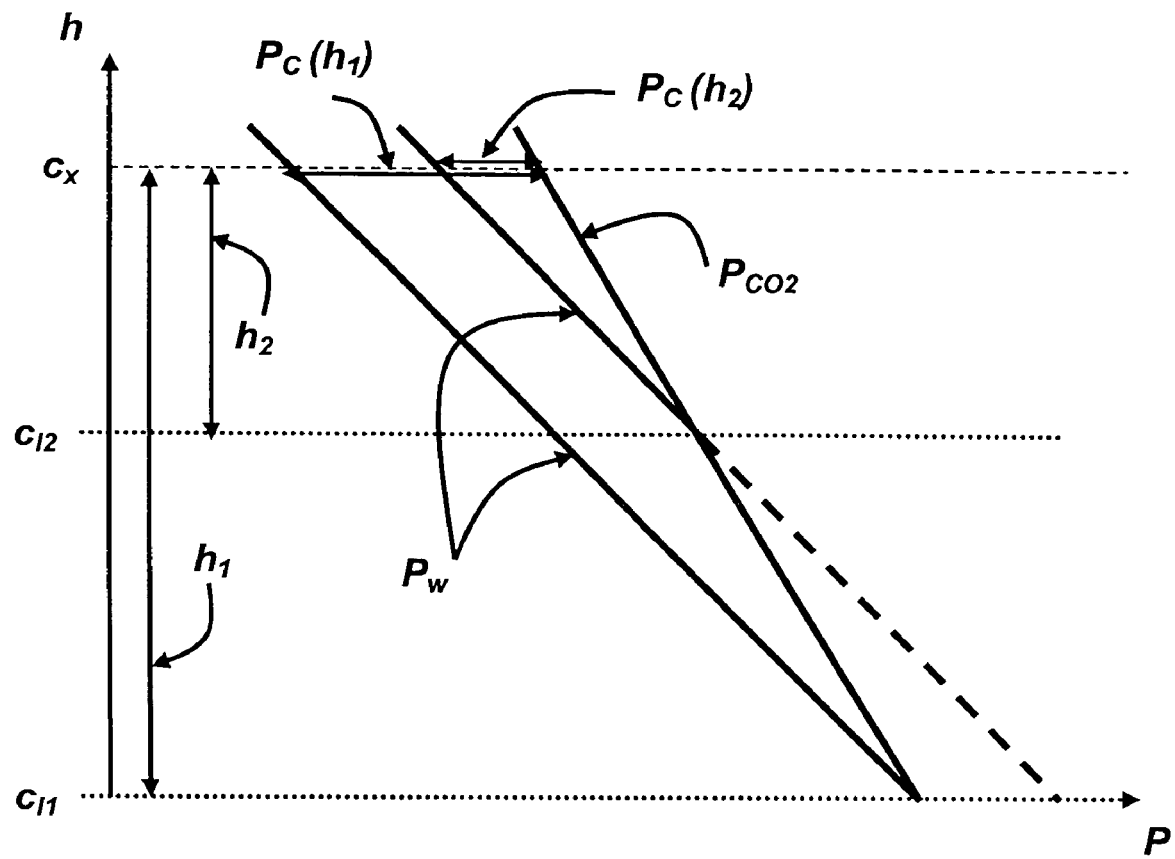
FIG. 1 illustrates the increase with time of the capillary pressure imposed at the top within the scope of a $CO_2$ storage operation.

The methods used in the profession and described above are essentially based on a "static" determination of the inlet capillary pressure value (semi-static for the residual capillary pressure method since we go through a transient flow phase), i.e. a fluid is injected, then stabilization of the outlet flow rate is monitored. From a more "dynamic" point of view, the inlet capillary pressure can also be considered to be a differential pressure between the two phases that does not contribute to the flow. Consider a sample initially saturated with a wetting fluid that is caused to flow by injecting a non-wetting fluid with a total differential pressure on the sample that is constant and equal to $DP_t$. The pressure profile can then be split up into several parts according to the nature of the phases present in the various parts of the sample:

$$DP_t = P_g^{am} - P_w^{av} = P_g^{am} - P_g^{fr} + P_g^{fr} - P_w^{fr} + P_w^{fr} - P_w^{av}$$

with:
$DP_t$: the total differential pressure imposed on the sample
$P_g^{am}$: the gas pressure upstream from the sample (inlet face)
$P_w^{av}$: the water pressure downstream from the sample (outlet face)
$P_g^{fr}$: the gas pressure at the front (gas/water interface)
$P_w^{fr}$: the water pressure at the front (gas/water interface)

In the case considered above, the total differential pressure imposed on the sample can thus be split up into three terms:

$$DP_t = DP_g + P_c^{fr} + DP_w$$

with:
$DP_g$: the differential pressure (pressure drop) in the zone invaded by the gas
$DP_w$: the differential pressure (pressure drop) in the zone that is not invaded by the gas
$P_c^{fr}$: the capillary pressure drop at the front which corresponds to the inlet capillary pressure: $P_c^{fr} = P_c^E$.

We can therefore write:

$$DP_t = DP_g + P_c^E + DP_w$$

Consider the very beginning of the invasion of the medium by the gas (non-wetting fluid). We can then assume that:
the differential pressure in the gas zone ($DP_g$) is negligible considering the limited extent of this zone (and also considering the low viscosity of the fluid injected, as it is the case for $CO_2$ even under storage conditions); and
the differential pressure in the water ($DP_w$) corresponds to the effective pressure difference that leads to the production of liquid in the buret at the outlet. This differential pressure $DP_w$ can therefore be directly calculated from Darcy's law for the production flow rate measured at the outlet ($Q_w$) and a permeability value (K) measured otherwise by means of techniques known to specialists:

$$Q_w = \frac{K \cdot S}{\mu_w} \cdot \frac{DP_w}{L} \Rightarrow DP_w = \frac{\mu_w \cdot L}{K \cdot S} Q_w$$

with:
S: the section of the sample (known)
L: the length of the sample (known)
$\mu_w$: the dynamic viscosity of the water (known).

The method according to the invention thus allows one to evaluate the inlet capillary pressure $P_c^E$ by means of the expression as follows:

$$P_c^E = DP_t - DP_w$$

It is thus possible to determine the value of the inlet capillary pressure $P_c^E$ by injecting directly the non-wetting fluid (gas) and by measuring the effective flow rate of the wetting fluid at the outlet ($Q_w$), which allows one to calculate the differential pressure in this phase $DP_w$. The inlet capillary pressure ($P_c^E$) is then simply obtained by calculating the difference between the total differential pressure imposed on the sample ($DP_t$) and the value of the differential pressure in the wetting phase ($DP_w$).

Thus, the method according to the invention can be broken down into five major stages.

1—A non-wetting fluid, such as gas, is directly injected into a sample of section S and of length L, saturated with a wetting fluid, such as water, and constrained to a total differential pressure on the sample $DP_t$.

2—The total differential pressure imposed on the sample ($DP_t$) is measured and a curve representing the volume of the wetting fluid expelled at the sample outlet as a function of time is drawn. This curve is a line whose slope corresponds to the reference flow rate ($Q_{ref}$).

3—The effective flow rate of the wetting fluid at the sample outlet ($Q_w$), which corresponds to the new slope of the curve, is calculated from the previous curve and after a slope change thereof.

4—The differential pressure in the wetting phase $DP_w$ is calculated, for example, from Darcy's law and by means of the dimensions of the sample (L and S), the dynamic viscosity $\mu_w$, the permeability of the sample (K) and the effective flow rate of the wetting fluid at the sample outlet ($Q_w$).

5—The value of the inlet capillary pressure $P_c^E$ is determined by calculating the difference between the total differential pressure imposed on the sample ($DP_t$) and the value of the differential pressure in the wetting phase ($DP_w$): $P_c^E = DP_t - DP_w$.

Experimental implementation

A sample of the porous medium whose inlet capillary pressure is to be evaluated is first saturated with a wetting fluid, then placed in a test cell known to the man skilled in the art and described for example in patent FR-2,708,742 (U.S. Pat. No. 5,679,885). What is understood to be a porous medium is any medium having pores through which a fluid can flow. The porosity can therefore have any value.

This device allows multi-flow rate displacement experiments to be carried out on a sample (E) from a porous medium. This device is diagrammatically shown in FIG. 2. It comprises an elongate containment cell 1 that can be cylindrical, and which contains the sample to be tested E between two end pieces 7a and 7b. This cell is placed inside a thermostat-controlled enclosure (not shown) so as to subject the sample to be tested to a predetermined temperature T. At the outlet of one of the faces of cell 1, an outlet end piece 3 allows the expelled fluid to be sent to a system 4 allowing to determine the volume of wetting fluid expelled. At the opposite face, the device comprises an inlet end piece 5 allowing injection of a non-wetting fluid into sample (E). At the level of containment cell 1, the sample to be tested E is placed within a deformable sheath 6 and the assembly is arranged within enclosure. The annular space around sheath 6 is communicated with a source of fluid under pressure (not shown) so as to subject the sample to be tested to a predetermined pressure P. The device also includes at least one differential pressure detector $CDP_t$ between the inlet and the outlet of the sample, for measuring the differential pressure produced on the sample itself $DP_t$. The device can comprise several such detectors, referred to as CDP1, CDP2, . . . and arranged at a respective distance from the inlet face L1, L2, . . . .

The experimental conditions are representative of the storage conditions insofar as the thermodynamic conditions, the nature of the fluids used and the state of mechanical stress (confining pressure in the test cell) are respected.

Without local saturation and pressure measurement

According to a first embodiment, the total pressure is measured without carrying out local pressure and saturation measurements.

Unlike the "conventional" method for determining the inlet capillary pressure, a significant volume of wetting fluid, typically some cubic centimeters, can be kept in inlet end piece 5. The non-wetting fluid is then injected at an imposed pressure so that the total differential pressure $DP_t$ is higher than an "a priori" estimated inlet capillary pressure value. The wetting fluid saturating the sample is then caused to flow with two distinct periods as shown in FIG. 3:

Period 1: as long as the non-wetting fluid is located in the inlet end piece, the wetting fluid circulates with a motive gradient directly related to the imposed total differential pressure $DP_t$. A linear production curve whose slope corresponds to the flow rate calculated with Darcy's law for the $DP_t$ and which thus represents the reference flow rate ($Q_{ref}$) for the imposed total differential pressure during the test is thus obtained. The flow is a single-phase flow throughout the sample; and Period P2: as soon as the non-wetting fluid reaches the inlet face, the Differential pressure in the wetting fluid phase decreases by the value of the inlet capillary pressure and a decrease in the production slope at the outlet is immediately observed. This slope then corresponds to the effective flow rate of the wetting fluid at the sample outlet ($Q_w$) allowing one to calculate the differential pressure in the wetting phase $DP_w$.

Figure 3:
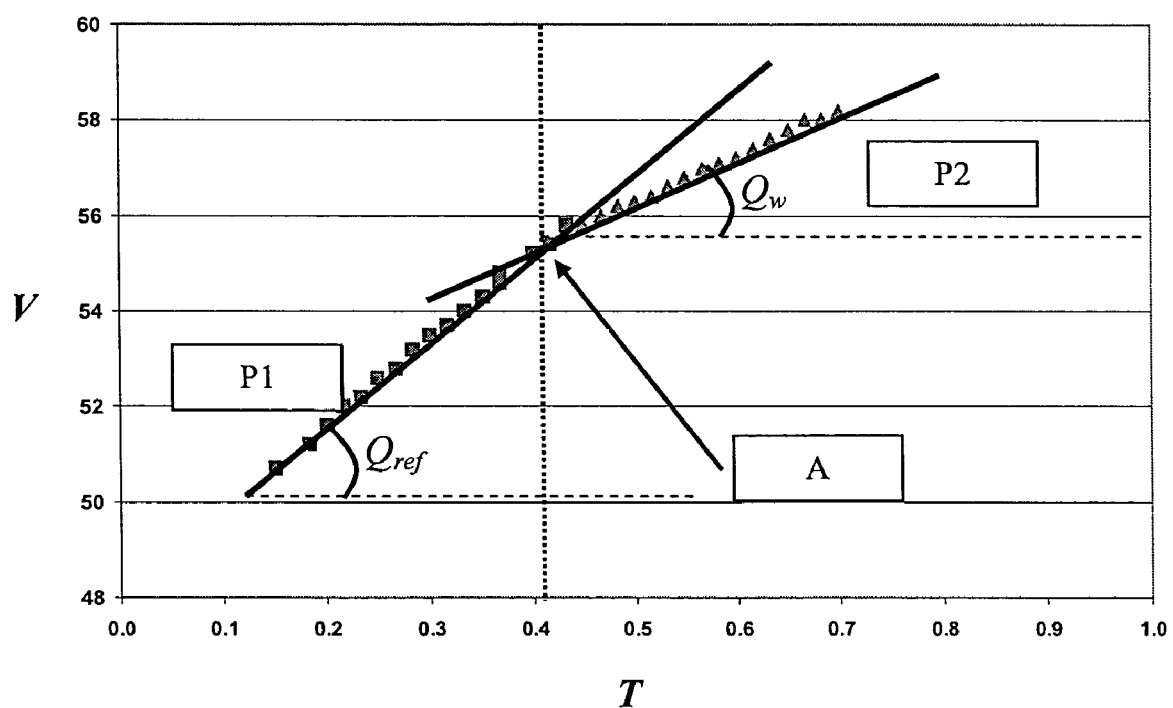
FIG. 3 shows a production curve obtained within the scope of the method proposed and underlines the flow rate change observed when the non-wetting phase starts saturating the sample (decrease in the slope of the production curve, therefore in the flow rate).

FIG. 3 shows a curve of the volume of fluid produced (V) as a function of time in hours (T) obtained within the scope of the method proposed. Two distinct slopes can be clearly seen, which correspond first to a strictly single-phase flow in the sample (P1), then to the arrival (A) of the non-wetting fluid at the inlet face, producing a reduction in the slope (P2) and therefore in the production flow rate ($Q_w$).

The presence of the volume of wetting fluid initially located upstream from the sample is not a prerequisite within the scope of the interpretation but it contributes to the quality control of the test carried out since it allows one to establish the reference flow rate ($Q_{ref}$) just before the non-wetting fluid starts flowing through the sample.

It can furthermore be noted that if the value of $DP_t$ was selected in a too conservative way (typically below the inlet capillary pressure value), the non-wetting fluid will stop at the inlet face without compromising the success of the test. In this case, the value of $DP_t$ just has to be significantly increased to carry the test through to completion.

With local saturation and pressure measurement

Figure 2:
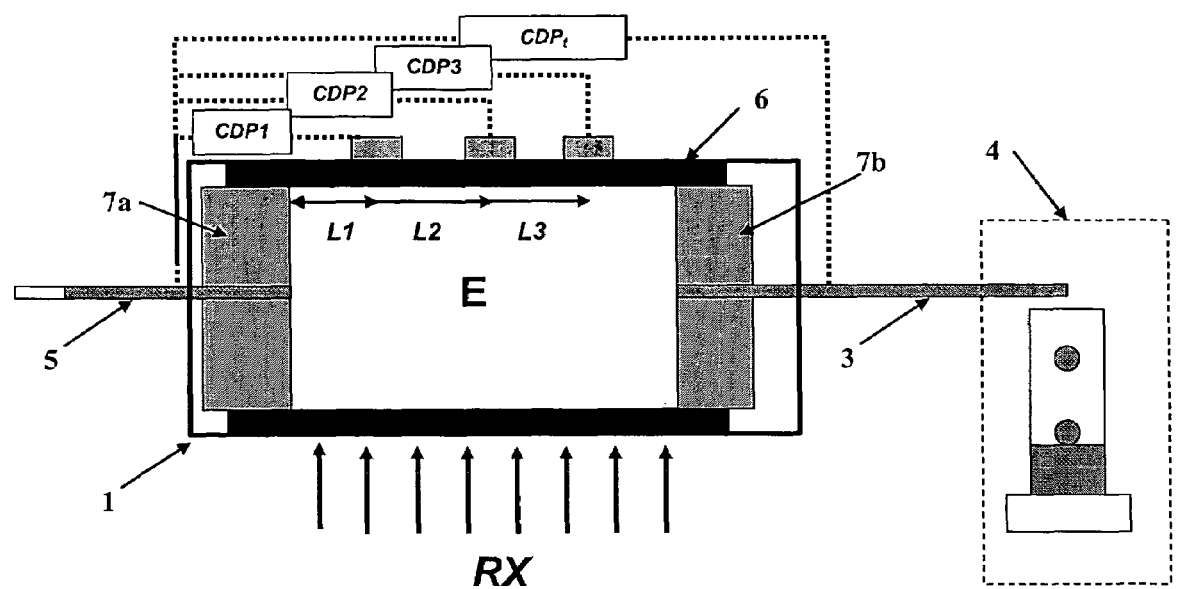
FIG. 2 shows the experimental device used to evaluate the dynamic inlet capillary pressures according to the invention.

According to another embodiment, a measurement of the total differential Pressure and local pressure and saturation measurements are carried out. If the test cell is provided with instrumentation allowing local pressure measurements to be performed along the sample and with a device allowing the saturation profile to be measured, it is possible to carry on with the degree of interpretation. This device is also shown in FIG. 2.

In fact, as long as the gas front located by means of the saturation measurement, by X-rays for example (RX), is upstream from the local pressure measuring points, each one of these points can be used to apply the previous approach "locally". The following formulas are then used, i representing the number of the local pressure detector used and $L^i$ the distance from the inlet face and the position of the detector considered:

$$Q_w = \frac{K \cdot S}{\mu_w} \frac{DP_w^i}{L^i}$$

$$P_c^E = DP_t^i - DP_w^i$$

This approach thus allows, with a single experimentation, to obtain several values for the inlet capillary pressure of a sample, which improves determination of this parameter while giving an error range for the result obtained. This is particularly useful within the scope of larger-scale studies intended to evaluate the associated uncertainties and risks as regards a storage site.

The table hereafter allows one to compare the three methods mentioned for three different rocks (R1, R2 and R3):

|    | Type      | K (mD) | Porosity (%) | $P_c^E$ conventional | $P_c^E$ residual | $P_c^E$ dynamic |
|----|-----------|--------|--------------|---------------------|------------------|-----------------|
| R1 | Chalk     | 1.7    | 40           | 0.9                 | 0.2              | 0.8             |
| R2 | Carbonate | 0.016  | 14.5         | 6                   | 3.1              | 6.2             |
| R3 | Sandstone | 0.0014 | 13           | 10                  | 7.7              | 9.6             |

It can be seen that the method according to the invention provides results that are comparable to those of the conventional method. These results are however more accurate and they were obtained more rapidly than those of the conventional method.

The invention claimed is:

1. A method for performing at least an evaluation of the inlet capillary pressure value of a porous medium, from a displacement experiment wherein a first fluid saturating a sample of said medium is caused to flow by injection of a second fluid at the level of a face of the sample referred to as "inlet" face, characterized in that said method comprises the following stages:

applying to the sample a constant pressure allowing said second fluid to flow into said sample;

drawing a curve of the volume of the first fluid expelled from said sample as a function of time;

continuously measuring as a function of time a local differential pressure $DP_t^i$ between said inlet face and at least one point located at a distance $L_i$ from the inlet face, this distance being greater than the distance between said inlet face and an interface between the two fluids within the sample;

calculating at least one differential pressure of the first fluid $DP_w^i$ by means of distance $L_i$ and of said curve; and determining at least one inlet capillary pressure value from local differential pressure $DP_t^i$ and the differential pressure value $DP_w^i$ of the first fluid.

2. A method as claimed in claim 1, wherein the value of the inlet capillary pressure is equal to the difference between local differential pressure $DP_t^i$ and the differential pressure $DP_w^i$ of the first fluid.

3. A method as claimed in claim 1, wherein the differential pressure value $DP_w^i$ of the first fluid is calculated after a slope change of said curve and by determining this new slope.

4. A method as claimed in claim 1, wherein distance $L_i$ is equal to the length of the sample and only the total differential pressure $DP_t$ between said inlet face and an opposite face of the sample is measured.

5. A method as claimed in claim 1, wherein the position of the interface between the two fluids is determined by carrying out local saturation measurements along the sample.

6. A method as claimed in claim 5, wherein several inlet capillary pressure values are determined and an uncertainty on the value of this inlet capillary pressure is deduced therefrom.

7. A method as claimed in claim 1, wherein a volume of first fluid is left upstream from the sample prior to starting injection of the second fluid.

8. A method as claimed in claim 1, wherein said displacement experiment is carried out under pressure and temperature conditions representative of the pressure and temperature conditions of oil reservoirs or of fluid storage sites.

9. A method as claimed in claim 1, wherein said first fluid is water.

10. A method as claimed in claim 1, wherein said second fluid is a gas.

11. A method as claimed in claim 1, applied to a porous medium of reservoir cap type, so as to evaluate the storage capacity of a reservoir intended for storage of a gaseous fluid.

12. A method as claimed in claim 1, applied to a porous medium of reservoir cap type, so as to evaluate the storage capacity of a reservoir intended for storage of a hydrocarbon.

13. A method as claimed in claim 1, applied to a porous medium of reservoir cap type, so as to evaluate the storage capacity of a reservoir intended for storage of $CO_2$.

* * * * *